US006685952B1

(12) United States Patent
Ma et al.

(10) Patent No.: US 6,685,952 B1
(45) Date of Patent: Feb. 3, 2004

(54) PERSONAL CARE COMPOSITIONS AND METHODS-HIGH INTERNAL PHASE WATER-IN-VOLATILE SILICONE OIL SYSTEMS

(75) Inventors: Zhuning Ma, Schaumburg, IL (US); Paul Howard Neill, Hinsdale, IL (US); Loralei Marie Brandt, Cary, IL (US); Anthony Aloysius Scafidi, Westchester, IL (US); Bozena Nogaj, Chicago, IL (US); Gerald Patrick Newell, Hoffman Estates, IL (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/344,014

(22) Filed: Jun. 25, 1999

(51) Int. Cl.[7] ............................. A61K 6/00; A61K 7/06
(52) U.S. Cl. ................... 424/401; 424/70.1; 424/70.12; 424/70.19
(58) Field of Search ................. 424/401, 455, 424/70.1, 78.02, 70.12, 70.19; 514/844, 880, 937, 938

(56) References Cited

U.S. PATENT DOCUMENTS

| | | |
|---|---|---|
| 4,057,622 A | 11/1977 | Hase et al. |
| 4,122,029 A | 10/1978 | Gee et al. |
| 4,151,204 A | 4/1979 | Ichikawa et al. |
| 4,218,250 A | 8/1980 | Kasprzak |
| 4,268,499 A | 5/1981 | Keil |
| 4,311,695 A | 1/1982 | Starch |
| 4,499,069 A | 2/1985 | Krafton |
| 4,784,344 A | 11/1988 | Lenk et al. |
| 4,948,578 A | 8/1990 | Burger et al. |
| 5,216,033 A | 6/1993 | Pereira et al. |
| 5,534,246 A | 7/1996 | Herb et al. |
| 5,587,153 A | 12/1996 | Angelone, Jr. et al. |
| 5,656,280 A | 8/1997 | Herb et al. |
| 5,688,831 A * | 11/1997 | El-Nokaly et al. ........... 514/938 |
| 5,849,310 A * | 12/1998 | Trinh et al. .................. 424/401 |
| 5,989,531 A * | 11/1999 | Schamper et al. ............. 424/65 |
| 6,143,286 A * | 11/2000 | Bhambhani et al. ........ 424/70.1 |

FOREIGN PATENT DOCUMENTS

| | | |
|---|---|---|
| EP | 0271925 | 6/1988 |
| EP | 0 379 677 | 8/1990 |
| EP | 0435483 | 7/1991 |
| EP | 0 490 582 | 6/1992 |
| EP | 0 595 683 | 5/1994 |
| EP | 0 638 308 | 2/1995 |
| JP | 2-167212 | 6/1990 |

* cited by examiner

Primary Examiner—Michael G. Hartley
(74) Attorney, Agent, or Firm—Milton L. Honig

(57) ABSTRACT

A composition which is:

A.) A hair care composition which is a high internal phase water-in-oil emulsion which comprises:
(I) an oil phase which further comprises i.) a mixture of non-volatile and volatile silicone oils, and ii.) a silicone surfactant; and
(II) which comprises an aqueous phase;
and which substantially lacks a fatty alcohol; and B.) A skin care composition which is a high internal phase water-in-oil emulsion which comprises:
(I) an oil phase which further comprises i.) a mixture of non-volatile and volatile silicone oils, and ii.) a silicone surfactant; and
(III) which comprises an aqueous phase.

30 Claims, No Drawings

PERSONAL CARE COMPOSITIONS AND METHODS-HIGH INTERNAL PHASE WATER-IN-VOLATILE SILICONE OIL SYSTEMS

BACKGROUND OF THE INVENTION

Typical hair conditioning products are usually based upon a cationic surfactant, generally a quaternary ammonium compound and fatty alcohol. This combination results in an oil-in-water lamellar gel-network that provides the formulation with a thick creamy rheology/viscosity. However, while such traditional compositions deliver conditioning benefits to the hair, the fatty alcohols and quaternary components also deposit onto the hair and continually build-up with each usage, making the hair look and feel weighed down and greasy.

The present invention is directed to a vehicle to deliver beneficial components to the hair and skin. The product forms for hair include leave-on or rinse-off conditioners, shampoos, hair color, and styling aids. The product forms for skin include leave-on or rinse-off skin care products such as lotions and creams.

The following are publications relating to this field of technology:
U.S. Pat. No. PATENT DOCUMENTS
  U.S. Pat. No. 4,311,695
  U.S. Pat. No. 4,122,029 Gee et al.
  U.S. Pat. No. 4,268,499
  U.S. Pat. No. 4,218,250
  U.S. Pat. No. 4,151,204
  U.S. Pat. No. 4,057,622
  U.S. Pat. No. 5,534,246 Herb et al., "Topically Effective Compositions" Jul. 9, 1996.
  U.S. Pat. No. 4,499,069
  U.S. Pat. No. 4,784,344
  U.S. Pat. No. 4,948,578 Burger et al.
  U.S. Pat. No. 5,216,033
  U.S. Pat. No. 5,587,153 Angelone, Jr. et al., "Clear, Gelled Aluminum and Zirconium Salt Containing Antiperspirant Formulation," Dec. 24, 1996.
FOREIGN PATENT DOCUMENTS
  EP 0,435,483
  EP 0,271,925
  JP 7-165529

SUMMARY OF THE INVENTION

The present invention is a high internal phase water-in-oil emulsion. High internal phase water-in-oil emulsions are defined as having greater than about 80% dispersed aqueous phase. The internal phase is defined as the non-continuous aqueous phase component of the emulsion. When compared to traditional oil-in-water conditioners, the hair is not weighed down as much by compositions of the present invention because fatty alcohols are not present in and are not deposited by the present hipe w/o formulations. The hipe water-in-oil conditioners thus leave the hair with a greater amount of natural volume, bounce and body. Previous water-in-oil emulsion systems known to those in the art of formulating hair and skin care products typically have dispersed water phases less than 80%. By contrast, the hipe water-in-oil emulsions systems of the present invention tend to deposit less silicone oil on the hair surface leading to improved rinsing and less greasiness and better overall dry hair aesthetics.

The present high internal phase water-in-oil emulsions (hipes) show superior aesthetic properties on skin by releasing the silicone oil more readily when compared to previous lower-internal phase water-in-oil systems (lipes), thereby giving the impression of easier spreading and quicker absorption on the skin surface. Hipes can be utilized for easier application and absorption when compared to lipes.

In the case of skin or hair leave on products, an ideal composition for the delivery of a topically-active compound to the skin or hair would be one that delivers the topically-active agent such that it adheres to the skin or hair while the topically-inactive ingredients evaporate or are removed from the site. Topically delivered active compounds, such as topical medicines or skin care compounds, have conventionally been formulated as either oil-in-water emulsions or water-in-oil emulsions. However, prior topical compositions prepared as these emulsions typically felt wet, sticky and tacky when applied to the skin substrate. Topical effective compositions should preferably possess the properties of smoothness, non-oiliness, and non-tackiness. In addition, the topically effective compositions should not have a wet feel. Therefore, it would be desirable to provide aesthetic benefits for non-greasy, non-sticky, non-wet feeling in topically effective compositions. The hipes can be utilized with sunscreen or anti-wrinkle agents or reactive agents.

A second disadvantage of typical hair and skin emulsion compositions is the complex preparation methods. The method traditionally requires high processing temperatures, and a series of heating or cooling steps. By contrast, the present invention, is prepared by a simple process without heating or cooling. The invention can also be made clear through the simple technique of refractive index matching. The present invention provides topically effective compositions which overcome the above-described difficulties and disadvantages of prior hair and skin emulsion compositions.

The present invention is directed to providing lotion or gel-type topically effective compositions, which exhibit these consumer acceptable aesthetic properties as well as functional properties.

The present invention also is suitable for application to skin as a lotion, cream or gel and may also contain topically active components such as but not limited to ultraviolet absorbers (sunscreens) or alpha hydroxy acids. The present invention also addresses improving upon the oiliness or greasiness of such products through the use of the high internal phase inverse water-in-oil emulsions. For example, in U.S. Pat. No. 5,216,033 and EP 435,483 A2, Pereira described examples of water-in-silicone skin care lotions. However, these prior formulations were more difficult to spread, felt more greasy, had greater residue and were more difficult to absorb into the skin (See Table 5).

BRIEF SUMMARY OF THE INVENTION

The invention is directed to a topical composition selected from the group consisting of:
  A.) A hair care composition which is a high internal phase water-in-oil emulsion which comprises:
    (I) an oil phase which further comprises i.) a mixture of non-volatile and volatile silicone oils, and ii.) a silicone surfactant; and
    (II) which comprises an aqueous phase;
      and which substantially lacks a fatty alcohol; and B.) A skin care composition which is a high internal phase water-in-oil emulsion which comprises:
  (I) an oil phase which further comprises i.) a mixture of non-volatile and volatile silicone oils, and ii.) a silicone surfactant; and
  (II) which comprises an aqueous phase.

More specifically, the present invention is directed to a hair care or skin composition which is a high internal phase water-in-oil inverse emulsion having improved efficacy, and to methods of using the high internal phase emulsion compositions. More particularly, the present invention is directed to a high internal phase water-in-silicone oil emulsion comprising a continuous external oil phase and an aqueous internal phase.

The continuous oil phase contains a silicone surfactant, and volatile and non-volatile silicone oils. The internal aqueous phase comprises water.

The compositions of the present invention comprise a high internal water phase emulsion, with a non-volatile silicone and a volatile, hydrophobic component suitable for application to either hair or skin. In particular, the present invention relates to hair and skin compositions comprising a high internal water phase emulsion which comprises: (1) less than about 20% of a continuous oil phase comprising (a) silicone surfactant or mixtures thereof; (b) a volatile oil and (2) at least about 80% of an aqueous internal phase and methods of treating the hair or skin.

It is the objective of the present invention to provide personal care compositions, having lower levels of oil phase, that offer advantages for both skin and hair care. The advantages for rinse-off hair care products include the ease of rinsing and leaving the hair with more of its natural body. Advantages for leave-on hair products and skin care products include less heaviness, less greasiness, less sticky and less tacky feel and leaving the hands free of residue when compared to typical water-in-oil skin formulations.

By utilizing low levels of silicone surfactant and very volatile dimethicones, the formulations of the invention have been able to overcome the difficulty of rinsing out the formulation from the hair.

High internal phase emulsions (HIPEs or hipes) may also be utilized in styling type leave-in products alone or in combination with polymers (DMAEMA, etc.) or structuring compounds (cellulosics, polysaccharides), etc. in order to provide control and hair manageability with a very clean, natural feel (nonsticky).

High internal phase emulsions (HIPES) may also be utilized in various shampoos, curling (straightening) or oxidative products along with the appropriate surfactants or reactive agents, respectively without resoiling and debodifying effects of fatty alcohol compounds.

High internal phase emulsions (HIPES) may also be utilized in skin care products such as lotions, wrinkle cream and sunscreens. The preparation and use of such products would be by methods materials known in the art or analogous to those known methods and materials.

An idea behind using a HIPE as an Extra Body Conditioner is that very little material is left behind on the hair to weigh it down after rinsing. By using a low level of silicone surfactant in combination with a dimethicone having a boiling point about that of room temperature (0.65cts) and a dimethicone of slightly higher viscosity for conditioning, the compositions of the invention rely as much on evaporation as rinsing for removal from the hair after conditioning.

The invention also comprises a method of treating hair which comprises contacting said hair with a composition of the invention. The invention also comprises a method of treating skin or the underarm which comprises contacting the skin or underarm with a composition of the invention.

DETAILED DESCRIPTION OF THE INVENTION

As used herein % means weight % unless otherwise noted. When it is said herein that a composition substantially lacks fatty alcohol, this means that said composition has less than about 1% fatty alcohol.

Compositions of the invention may be made with known starting materials or with starting materials that can be made by known methods. Compositions of the invention can be made by known methods or by methods which are analogous to known methods.

High internal phase water-in-oil emulsions (hipes) may be utilized in styling type leave-in products alone or in combination with polymers or structuring compounds in order to provide control and hair manageability with a very clean, natural, nonsticky feel.

High internal phase water-in-oil emulsions (hipes) may also be utilized in various shampoos, conditioners, styling, curling, waving, straightening, coloring, or oxidative products along with the appropriate surfactants or reactive agents, respectively without the resoiling and debodifying effects of fatty alcohol compounds and without waxy feel upon the hair.

The internal or aqueous phase can comprise from about 80% to about 95% of the composition, or more preferably from about 85% to 90%. The invention also comprises a method of treating hair which comprises contacting said hair with a composition of the invention.

As noted above in the present invention, the compositions have both high viscosity and opacity through the use of a high internal phase water-in-oil emulsion. These compositions deliver conditioning agents onto the hair.

Another aspect of the invention is to provide a method of treating the hair to yield well-conditioned hair having esthetically pleasing physical properties by contacting the hair with an opaque conditioner of the present invention.

Another aspect of the invention is to provide a conditioning composition that is easy to rinse from the hair. The compositions of the invention are easy to rinse from the hair due to the presence of either volatile silicones, polymers, surfactants or other compounds which may alter the deposition upon the hair.

The invention is directed to a topical composition selected from the group consisting of:
  A.) A hair care composition which is a high internal phase water-in-oil emulsion which comprises:
    (I) an oil phase which further comprises i.) a mixture of non-volatile and volatile silicone oils, and ii.) a silicone surfactant; and
    (II) an aqueous phase;
    and which substantially lacks a fatty alcohol; and
  B.) A skin care composition which is a high internal phase water-in-oil emulsion which comprises:
    (I) an oil phase which further comprises i.) a mixture of non-volatile and volatile silicone oils, and ii.) a silicone surfactant; and
    (II) an aqueous phase.

Ingredients that are used in the preparation of compositions of the invention are now described.

Silicone Surfactants

Exemplary of the silicone surfactants or emulsifiers that are used in compositions of the invention is a dimethicone, which is a dimethylsiloxane polymer having polyoxyethylene and/or polyoxypropylene side chains, such as DOW CORNING 3225C and 5225C FORMULATION AID, available from Dow Corning Co., Midland, Mich., SILICONE SF-1528, available from General Electric, Waterford, N.Y., ABIL EM 97, available from Goldschmidt Chemical Corporation, Hopewell, Va. and SILWET™ series, available from OSI Specialties, Inc., Danbury, Conn. The dimethicone copolyol has about 15 or fewer ethylene oxide and/or propylene oxide monomer units, in total, in the side chains. Dimethicone copolyols conventionally are used in conjunction with silicones because the oil-soluble, silicon-based surfactants are extremely soluble in a volatile or a nonvolatile silicone compound, are extremely insoluble in water. These products have the following general formula:

$$Me_3SiO(Me2SiO)_x(MeSiO)_ySiMe_3$$
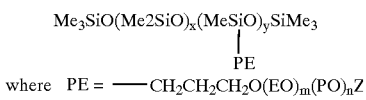

where PE = —$CH_2CH_2CH_2O(EO)_m(PO)_n Z$

In this formula, Me represents methyl, EO represents ethyleneoxy, PO represents 1,2-propyleneoxy, x and y are 1 or greater, m and n can be 0 or greater, however the molecular weight of the PE unit must be greater than 1000, and Z can be either hydrogen or a lower alkyl radical.

Suitable silicone surfactants for use in compositions of the invention are disclosed in U.S. Pat. No. 4,122,029 to Gee which is, hereby incorporated by reference.

Another exemplary, but nonlimiting, oil-soluble, silicon-based surfactant is an alkyl dimethicone copolyol, such as cetyl dimethicone copolyol available commercially as ABIL EM 90 from Goldschmidt Chemical Corporation, Hopewell, Va. The alkyl dimethicone copolyols have the structure:

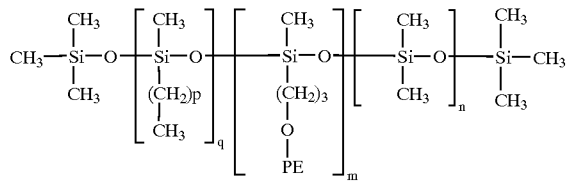

wherein p is a numeral from 7 through 17;
q is a numeral from 1 through 100;
m is a numeral from 1 through 40;
n is a numeral from 0 through 200; and
PE is $(C_2H_4O)_a(C_3H_6O)_b$—H having a molecular weight of about 250 to about 2000, wherein a and b are selected such that the weight ratio of $C_2H_4O/C_3H_6O$ is from 100/0 to 20/80.

Volatile Silicone Oils which are included in compositions of the invention

The silicone oil phase of the compositions of the invention comprises a mixture of a volatile silicone oil, and a nonvolatile silicone oil. Exemplary volatile silicone compounds include, but are not limited to, volatile, low molecular weight polydimethylsiloxane compounds. They can be either a linear or a cyclic polydimethylsiloxane compound having a viscosity from about 0.5 to about 10 cst (centistokes). The preferred linear polydimethylsiloxane compounds can have a viscosity range from about 0.5 to 10 cst. The preferred volatile polydimethylsiloxanes have a viscosity in the range of about 0.5 to about 6 cst.

The cyclic, volatile, low molecular weight polydimethylsiloxanes, designated in the CTFA Dictionary as cyclomethicones, are the preferred siloxanes used in a composition of the present invention. The cyclic volatile siloxanes can be either D4, D5 or D6, and mixtures thereof); boil at atmosphere pressure at from about 35° C. to about 250° C. The polydimethyl cyclosiloxanes having an average of about 4 to about 5 repeating units per molecule are especially preferred. Suitable cyclomethicones are available commercially under the trade names DOW CORNING 244 Fluid, DOW CORNING 245 Fluid, DOW CORNING 344 Fluid and DOW CORNING 345 Fluid from DOW CORNING Corporation, Midland, Mich., and SILICONE SF-1173 and SILICONE SF-1202 from General Electric, Waterford, N.Y.

An example of a linear, low molecular weight, volatile polydimethylsiloxane compound is designated in the CTFA Dictionary as decamethyltetrasiloxane, available commercially under the trade names DOW CORNING 200 Fluid having a viscosity of 1.5 cst and a boiling point of 195° C. Other linear polydimethylsiloxanes include octamethyltrisiloxane, and decamethylpentasiloxane which also be useful in the composition of the present invention.

Volatile Hydrocarbon Oils which are optional but which may be included in compositions of the invention The volatile hydrocarbon oil phase comprises about 6 to 20 carbon atoms. A preferred volatile hydrocarbon compound is an aliphatic hydrocarbon having about 8 to 16 carbon atoms, and having a boiling point of about 100 to 250° C. Exemplary volatile hydrocarbon compound include, isododecane and isohexadecane, i.e., PERMETHYL 99A, PERMETHYL 101A, available from Presperse, Inc., South Plainfield, N.J. Other examples are depicted in general structure formula (I), wherein n ranges from 2 to 3.

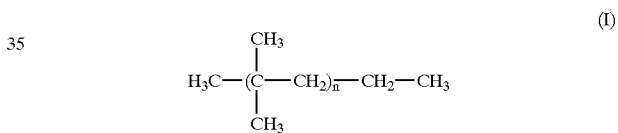

Another exemplary volatile hydrocarbon compound is ISOPAR M (a $C_2$–$C_{14}$ isoparaffin available From EXXON Chemical Co., Baytown, Tex.).

Non-volatile Silicone compounds which are included in compositions of the invention Exemplary nonvolatile silicone compounds include a polydimethylsiloxane, polyalkyl siloxane, a polyaryl siloxane or a polyalkylaryl siloxane. The nonvolatile silicones are nonfunctional siloxanes or siloxane mixtures having a viscosity of about 10 to about 10,000 cst, and most preferred viscosity about 10 to 500 cst at 25° C. A nonvolatile silicone compound is described as having a boiling point at atmospheric pressure of greater than about 250° C. A phenyltrimethicone also is useful as a nonvolatile silicone compound. An example includes DC 556 fluid, which is available from Dow Corning.

Non-volatile hydrocarbon compounds which may or may not be included in compositions of the invention The nonvolatile oil phase also can comprise a nonvolatile hydrocarbon compound, such as mineral oil, or isoeicosane. Other exemplary compounds include a water insoluble emollient, such as, for example, an ester having at least about 10 carbon atoms, and preferably about 10 to about 32 carbon atoms. Suitable esters include but are not limited to, for example, aliphatic monohydric alcohol esters including isopropyl myristate and aliphatic di- or tri-esters of polycarboxylic acids including dioctyl adipate.

Examples of optional compounds which can be included in compositions of the invention Exemplary classes of such compounds includes di-long chain alkyl amines (i.e. $C_{10}$ to $C_{22}$), long chain fatty alpine (i.e. $C_{10}$ to $C_{22}$), long chain fatty alcohols (i.e. $C_{10}$ to $C_{22}$), ethoxylated fatty alcohols, and double-tailed phospholipids. Specific compounds capable of participating in the formation of a lamellar dispersed phase, include dipalmitylamine, stearamidopropyldimethylamine. cetyl alcohol, stearyl alcohol, steareth-2, steareth-21, phosphatidylserine, phosphatidylcholine, and mixtures thereof.

Optional cationic surfactants may be used so long as they are miscible in the compositions of the invention. The optional cationic surfactants can have the structure:

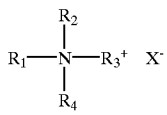

wherein $R_1$ is an alkyl group including from about 8 to about 20 carbon atoms; $R_2$ is selected from the group consisting of an alkyl group including from about 8 to about 20 carbon atoms, a hydrogen atom, a methyl group, an ethyl group, a hydroxymethyl group and a hydroxyethyl group; $R_3$ is selected from the group consisting of a benzyl group, a hydrogen group, a methyl group, an ethyl group, a hydroxymethyl group and a hydroxyethyl group; $R_4$ is selected from the group consisting of a hydrogen atom, a methyl group, an ethyl group, a hydroxymethyl group and a hydroxyethyl group; and X is an anion. The quaternary nitrogen of the water-soluble quaternary ammonium compound also can be a component of a heterocyclic nitrogen-containing moiety, such as morpholine or pyridine. The anion of the quaternary ammonium compound can be any common anion, such as chloride, methosulfate, ethosulfate, nitrate, bromide, tosylate, acetate, or phosphate, and mixtures thereof.

The optional water-soluble quaternary ammonium compounds have one or two long chain alkyl groups containing from about 8 to about 18 carbon atoms. The long chain alkyl groups also can include, in addition to, or in replacement of, carbon and hydrogen atoms, ether linkages or similar water-solubilizing linkages. The remaining two or three substitutes of the quaternary nitrogen of the quaternary ammonium compound can be hydrogen; benzyl; or short chain alkyl or hydroxyalkyl groups, such as methyl, ethyl, hydroxymethyl or hydroxyethyl groups; or combinations thereof, either of the same or different identity.

Exemplary water-soluble quaternary ammonium compounds include, but are not limited to, lauryltrimonium chloride; Quaternium-16; laurylalkonium chloride; olealkonium chloride; dilauryldimonium chloride; cetalkonium chloride; dicetyldimonium chloride; laurylpyridinium chloride; cetylpyridinium chloride; soyatrimonium chloride; Polyquaternium-6; Polyquaternium-7; guarhydroxypropyltrimonium chloride; polyquaternium-11; polyquaternium-5; polyquatemium-10; polyquaternium-24; polyquaternium-37, cetrimonium chloride; Quaternium-24; mytrimonium chloride; PEG-2 cocomonium chloride; PEG-2 cocoyl quaterrium 4; PEG-15 cocoyl quaternium 4; PEG-2 stearyl quatemium 4; PEG-15 stearyl quatemium 4; PEG-2 oleyl quaternium 4; PEG-15 oleyl quaternium 4, and mixtures thereof, wherein the compound designation is provided by the Cosmetic, Toiletry and Fragrance Association, Inc. in the CTFA Cosmetic Ingredient Dictionary, 4th Ed., 1991, hereinafter referred to as the CTFA Dictionary. Other water-soluble quaternary ammonium compounds are listed in the CTFA Cosmetic Ingredient Handbook, 1st Ed., 1988 (hereinafter the CTFA Handbook) at page 40–42, incorporated herein by reference.

Other optional ingredients included in compositions of the invention may be paraffin, isoparaffin, beeswax, microcrystalline wax, ozokerite wax, carnauba wax, candelilla wax, vaseline solid paraffin, squalene, oligomer olefins and the like; amidoamines such as stearamidopropyl dimethylamine, isostearamidoethyl morpholine, behenamidopropyl dimethylamine and the like; humectants such as glycerine, propylene glycol, glycerol, sorbitol and the like; esters, such as isopropyl palmitate, isopropyl myristate, and stearyl stearate and the like; emulsifiers such as glyceryl monostearate, sorbitan monopalmitate, polyoxyethylene stearate and the like.

Optional holding polymers of the present invention include vinyl and acrylic-based resins such as Copolymer 845, 937 and 958, a vinyl pyrrolidone/dimethylaminoethyl methacrylate copolymer, Styleze CC-10, a PVP/DMAPA Acrylates Copolymer, Polymer 1189 (Terpolymer of Vinyl pyrrolidonenVinyl Caprolactam and 3-(N-Dimethylaminopropyl) Methacrylamide, all of which are available from International Specialty Products; Gafquat polymers 734 and 755N designated as Quatemium-23, Gantrez ES-425 is the butyl ester of PVM/MA copolymer, all supplied by International Specialty Products, PVP K-30 to K-90, a polyvinylpyrollidone of various molecular weights, obtained from BASF, Flexan 130, a Sodium Polystyrene Sulfonate, obtained from National Starch, Amphomer 28-4910, an Octylacrylamide/acrylates/butylamino methacrylate copolymer supplied by National Starch, Amphomer LV-71, Octylacrylamide/Acrylates/Butylaminoethyl Methacrylate Copolymer, Balance 0/55, a Methacrylate polymer, Versatyl-42, an Acrylates/Octylacrylamide Copolymer, Resyn 28-2930 is VA/Crotonates/Vinyl Neodecanoate Copolymer and Lovocryl-47, an Octylacrylamide/Acrylates/Butylaminoethylmethacrylate Copolymer, Amaze Starch Polymer, all supplied by National Starch, Polyether Polyurethanes are available from Tyndale Plains Hunter, polyurethanes from IDPI, Luviset PUR polyurethanes from BASF, acrylates copolymers, acrylamide copolymers, acrylamide/sodium acrylate copolymer, acrylate/ammonium methacrylate copolymer, acrylate copolymers, acrylic/acrylate copolymers, acrylic esters and methacrylic esters copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer. ammonium acrylate copolymers, ammonium vinyl acetate/acrylate copolymers, AMP acrylate/diacetoneacrylamide copolymers, AMPD acrylate/diacetoneacrylamide copolymers, butylated PVP, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, diglycoL/cyclohexanedimethanol/Isophthalates/sulfoisophthalates AQ 55S polymer, diglycol/isophthalates/sulfoisophthalates copolymer AQ29S polymer, dodecanedioic acid/cetearyl alcohoUglycol copolymer, ethyl ester of PVM/MA copolymer, isopropyl ester of PVMJMA copolymer, Graft-copoly(dimethylsiloxane iso-butyl methacrylate), Graft-copoly (IBMA;MEFOSEA/PDMS), methacrylates/acrylates copolymer/amine salt, methacryloyl ethyl betaine/methacrylate copolymers, octylacryl-amide/acrylate/butylaminoethyl methacrylate copolymers, octylacrylamide/acrylate copolymers, phthalic anhydride/ glycerin/glycidyl decanoate copolymer, phthalic/trimellitic/ glycol copolymers, polyacrylamide, polyacrylamidomethylpropane sulfonic acid, polybutylene terephthalate, polyethylacrylate, polyethylene, polymethacrylamidopropyl trimonium chloride, polyquatemium-1, polyquaternium-2, polyquaternium-4, polyquaternium-5, polyquaterium-6, polyquaterium-7, polyquatemium-8, polyquaternium-9, polyquaternium-10, polyquaternium-11, polyquaternium-12, polyquaternium-13, polyquaternium-14, polyquaternium-15, polyquaterium-16, polyquaternium-24, polyquaternium-28, polyquaternium-37, polyquaternium-46, polyvinyl acetate, polyvinyl butyral, polyvinyl imidazolinium acetate, polyvinyl methyl ether, ethyl ester of poly (methyl vinyl ether/maleic acid, butyl ester of poly (methyl vinyl ether/maleic acid, PVM/MA copolymer, PVP, PVP/ acrylates copolymer, PVP/dimethylaminoethylmethacrylate terpolymer, PVP/eicosene copolymer, PVP/ethyl methacrylate/methacrylic acid copolymer, PVP/hexadecane copolymer, PVP/VA copolymer, PVP/VA/vinyl propionate copolymer, PVP/vinyl acetate copolymer, PVP/vinyl acetate/itaconic acid copolymer, quaternium-23, shellac, sodium acrylate/vinyl alcohol copolymer, sodium carrageenan, starch diethylaminoethyl ether, stearylvinylether/maleic anhydride copolymer, sucrose benzoate/sucrose acetate isobutyrate/butyl benzyl phthalate copolymer, styrene/PVP copolymer, sucrose benzoate/ sucrose acetate isobutyrate/butyl benzyl phthalate/methyl methacrylate copolymer, sucrose benzoate/sucrose acetate iso-butyrate copolymer, Tricontanyl PVP, vinyl acetate/ crotonate copolymers, vinyl acetate/crotonic acid copolymer, vinyl acetate/butyl maleate/Isobornyl acetate copolymer, vinyl acetate/crotonic acid/ methacryloxybenzophenone-1 copolymer, vinyl acetate/ crotonic acid/vinyl neodecanoate copolymer, vinyl caprolactam/PVP/Dimethylaminoethyl methacrylate copolymer, and mixtures thereof.

Optional saccharides which may optionally be used in the present invention include nonionic or cationic saccharides such as cellulose ethers including methyl cellulose, carboxymethyl cellulose, hydroxy propyl methyl cellulose, hydroxyethyl cellulose, hydroxypropyl cellulose, and ethyl hydroxyethyl cellulose, dextrans obtained from Sigma, Kitamer PC, a chitosan carboxylate and Kytamer L, a chitosan lactate obtained from Amerchol, Gafquat HS-100, Polyquaternium-28 from International Specialties, polyquaternium-4, polyquaternium-10, sodium alginate, agarose, amylopectins, amyloses, arabinans, arabinogalactans, arabinoxylans, carrageenans, gum arabic, cellulose derivatives such as methylcellulose, hydroxypropylmethylcellulose, hydroxyethyl cellulose, carboxymethylcellulose, carboxymethylguar gum, carboxymethyl(hydroxypropyl)guar gum, hydroxyethylguar gum, hydroxypropylguar gum, cationic guar gum, chondroitins, chitins, chitosans, cocodimonium hydroxypropyl oxyethyl cellulose, colominic acid [poly(N-acetylneuraminic acid], corn starch, curdlan, dermatin sulfate, furcellarans, dextrans, cross-linked dextrans known as dextranomer (Debrisan), dextrin, emulsan, flaxseed saccharide (acidic), galactoglucomannans, galactomannans, glucomannans, glycogens, guar gum, or hydroxyethylstarch, hydroxypropylstarch, hydroxypropylated guar gums, gellan gum, glucomannans, gellan, gum ghatti, gum karaya, gum tragacanth (tragacanthin), heparin, hyaluronic acid, inulin, keratan sulfate, konjac mannan, laminarans, laurdimonium hydroxypropyl oxyethyl cellulose, liposan, locust bean gum, mannans, nigeran, nonoxylnyl hydroxyethyl cellulose, okra gum, oxidized starch, pectic acids, pectins, polydextrose, potato starch, protopectins, psyllium seed gum, pullulan, sodium hyaluronate, steardimonium hydroxyethyl cellulose, raffinose, rhamsan, tapioca starch, welan, levan, scleroglucan, stachyose, succinoglycan, wheat starch, xanthan gum, xylans, xyloglucans, and mixtures thereof. Microbial saccharides can be found in the fourth edition of Kirk-Othmer *Encyclopedia of Chemical Technology*, Fourth Edition. Vol. 16, John Wiley and Sons, NY pp. 578–611, 1994 which is herein incorporated by reference. Complex carbohydrates can be found in the fourth edition of Kirk-Othmer *Encyclopedia of Chemical Technology*, Fourth Edition. Vol. 4, John Wiley and Sons, NY pp. 930–948, 1994 which is herein incorporated by reference.

Thickeners can be utilized alone or in combination so long as the chosen thickeners are compatible with the compositions of the invention (that is, that they cause the compositions of the invention to thicken). Thickeners can include, for example, Acrylic acid homopolymers under the Carbopol name from BF Goodrich, acrylates/C10–30 alkyl acrylate crosspolymer (Carbopol 1342, 1382, Pemulins TR-1 and TR-2 from BF Goodrich), Acrylates/Steareth-20 Itaconate Copolymer, Acrylates/Ceteth-20 Itaconate Copolymer, National Starch, Bentonite, PVM/MA Decadiene Crosspolymer from International Specialties Products, Acrylates/steareth-20 methacrylate copolymer, Acrysol ICS-1, Rohm and Haas Co., acrylamide/sodium acrylate copolymer, Hostacerin PN 73, Hoecsht AG., acrylate copolymer (Antil 208) supplied by Goldschmidt, acrylic acid/acrylonitrogens copolymer (Hypan SA-100H, SR-150H) supplied by Lipo, Acrylic/acrylate copolymer (Carboset5 514, 515, 525, XL-19, XL-19X2, X1-28, XL-40, 526) supplied by BF Goodrich, Ammonium acrylates/ acrylonitrogens copolymer (Hypan SS-201) from Lipo, Quaternium-18 Bentonite, Sodium salt of crosslinked poly (acrylic acid) under the tradenames PNC 430, PNC 410, PNC 400 from 3V, Stearalkonium Bentonite, Claytone, supplied by Southern Clay, Quaternium-18 Hectorite (Bentone 38), Stearalkonium Hectorite (Bentone 27) supplied by Rheox, acrylamide/sodium acrylate copolymer (Hostacerin PN 73) supplied by Hoechst, Poly(acrylic acid) known as Carbopol 400 series (BF Goodrich) or Aquatreat (Alco 3V), polyquatemium-18 (Mirapol AZ-1) from Rhone Poulenc, polyquaternium-27, polyquaternium-3 1, polyquaternium-37, trihydroxystearin (Thixcin from Rheox; Flowtone from Southern Clay), Dimethylaminoethyl methacrylamide and acrylamide copolymer (Salcare SC63 from Ciba Specialties), Acrylic polymer anionic or cationic thickening agents (Synthalen CR and its related compounds) from 3V Sigma.

Other thickeners and polymers can be found in the "The Encyclopedia of Polymers and Thickeners for Cosmetics," *Cosmetics and Toiletries*, Lochhead, R., pp. 95–138, Vol. 108, (May 1993) which is herein incorporated by reference.

The compositions may also optionally contain a topically active agent selected from but not limited to para-aminobenzoic acid (PABA); PABA esters, such as glyceryl PABA, amyldimethyl PABA and octyldimethyl PABA; cinnamates, such as octyl methoxycinnamate, ethylhexyl para-methoxycinnamate, 2-ethoxyethyl para-methoxycinnamate and cinoxate, benzophenones, such as benzophenone-4, oxybenzone and sulisobenzone, salicylates, such as octyl salicylate, anthranilates, such as methyl anthranilate; and mixtures thereof.

The topically active compound may also be an alpha hydroxy acid having the following structure:

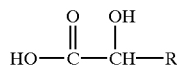

wherein R can be hydrogen or an alkyl from 1 to 28 carbons.

Further optional components can include, for example: pH adjusting agents, viscosity and rheology modifiers, pearlescers, opacifiers, suspending agents, bacteriocides, coloring agents, fragrances, ultraviolet protective agents, dyes, proteins, herb and plant extracts, polyols, and other moisturizing and/or conditioning agents.

The topically active compound may also be a hair growth promoter such as glucarolactams, glucarolactones, and diacylglycerols, and mixtures, thereof.

Compositions of the invention can take the form of leave-in or rinse out conditioners. They can also be shampoos or styling aids. Compositions of the invention can also be skin care products.

To use the rinse out compositions of the invention to condition hair, one first wets the hair, then applies the composition of the invention, next lathers the hair, and finally rinses the hair. Alternatively, water and conditioner may be applied to the hair simultaneously. Conditioning with compositions may be done right after shampooing when the hair is still wet. Alternatively, conditioning of the hair may be performed separately from shampooing on either wet or dry hair.

Compositions of the invention may be leave-in conditioners as mentioned above. In such cases, the compositions of the invention are usually worked into the hair usually by using the fingers.

Compositions of the invention may be used as shampoos by application to wet hair followed by lathering and rinsing. They may be used as styling aids in a conventional manner. They may also be used as skin care products in a conventional manner.

Compositions of the invention provide unexpectedly superior conditioner properties without the use of fatty alcohols.

Embodiments of the present invention will now be flirther illustrated by reference to the following examples and tables.

Compositions of the invention are made as follows:
1. The oil phase is mixed.
2. The aqueous phase is added slowly to the oil phase.

EXAMPLES

Examples of Wet Combing Force Data

| Composition | A Weight percent | B Weight percent | C Weight percent |
|---|---|---|---|
| Oil Phase | | | |
| DC 3225C | 0 | 4.00 | 5.70 |
| DC 5225C | 3.00 | 0 | 0 |
| DC 200, 10 cst | 0.67 | 0 | 0 |
| DC 200, 5 cst | 1.33 | 0 | 0 |
| DC 200, 1.5 cst | 2.00 | 6.50 | 6.90 |
| DC 200, 0.65 cst | 0 | 0 | 0 |
| DC 245 | 3.40 | 0 | 0 |
| Fragrance | 0.30 | 0 | 0 |

-continued

Examples of Wet Combing Force Data

| Composition | A Weight percent | B Weight percent | C Weight percent |
|---|---|---|---|
| Aqueous Phase | | | |
| Water | 89.00 | 85.20 | 83.20 |
| Salcare SC-96, 50% | 1.00 | 0 | 0 |
| Sodium Chloride | 0 | 4.00 | 3.90 |
| Preservative | 0.30 | 0.30 | 0.30 |
| Total | | | |
| Combing force (gm force) | 8.7 gm | 36.2 gm | 35.9 gm |

*Salcare SC-96 is polyquaternium-37/propylene glycol/dicaprylate dicaprate and PPG-1

Tidceth-6 available from Ciba Specialty Chemicals, Suffolk, Va.

Compositions A, B, and C above are all compositions of the invention. It is noted that the silicone surfactants DC 3225C AND DC 5225Care made up of a silicone surfactant and 80% of a volatile silicone such as D4 or D5.

Test 1—Instron Wet Combing

Wet combing experiments were carried out utilizing an Instron 5500 Series. All testing was carried out by applying 0.3 ml of product to bleached and waved 2 g hair tresses. Results are expressed in terms of maximum load (gm of force).

Conventional Body conditioners have an average 13.1 gm to about 40 gm of force, whereas Example A has improved combing forces of about 8.7 gm. Examples B and C have combing forces of about 36.2 and 35.9 gm, respectively in order to impart greater body, volume and stylability to the hair. In other words, the increase in wet combing force caused by compositions of the invention is an advantageous property. Further examples demonstrate the versatility of the invention. Products that vary in softness, body and conditioning levels appear below. All examples may be left upon the hair or rinsed out. These products may also be utilized on the skin as well.

Salon Testing

The following Salon Blitz Testing table is a summary of the results from a salon test conducted. The benchmark for these studies was a moisturizing conditioner product sold in the North American market. These data indicated that Example C outperformed the benchmark formulation in its ability to deliver hair body as reported by the models.

Test 2—Salon Blitz

Salon Blitz utilized female conditioner users as the panelists. A professional hair stylist applied the test product to half of the head and the benchmark product to the other side of the panelist's head. Once product has been applied, the stylist distributed the product evenly and left on the hair, keeping both sides separated. Product is then rinsed off after one minute. The panelists then dried and styled their own hair. A questionnaire was provided to each panelist asking them to rate (on a 9 point scale) hair characteristics for both the left and right side of the head. Higher values for key characteristics such as softness and fullness indicated a higher intensity for these attributes and therefore better performance on the hair. 20 panelists were recruited for each test product evaluation. Results for this test are shown in Table 1. The following Salon Blitz Testing table is a summary of the results from a salon test conducted. The benchmark for these studies was a moisturizing product sold in the North American market.

TABLE 1

Salon testing of Example C versus Benchmark Moisturizing Conditioner.

| Attribute | Example C | Moisturizing benchmark- a commercial product | Difference |
|---|---|---|---|
| Overall Liking | 6.83 | 6.42 | +0.41 |
| Body Added | 7.05 | 6.11 | +0.94 |
| Conditioning | 6.89 | 6.21 | +0.68 |
| Fullness | 7.11 | 6.00 | +1.11** |
| Bounce | 7.16 | 5.95 | +1.21** |
| Softness | 7.42 | 6.63 | +0.79 |
| Amt. Conditioning | 6.47 | 6.95 | +0.68 |
| Amt. Body | 6.47 | 5.68 | +0.79 |
| Coating | 3.53 | 4.47 | −0.94 |
| Amt. Bounce | 6.84 | 5.37 | +1.47** |
| Amt. Volume | 6.21 | 5.00 | +1.21** |
| Ease of Styling | 7.42 | 6.74 | +0.68 |
| Static | 2.16 | 3.16 | −1.00** |

*A positive difference noted enhanced performance except in the case for static and coating where "Less static" and "Less coating" is desirable.
**90% Confidence Level.

These data indicated that Example C outperformed the benchmark formulation in its ability to enhance hair body, bounce, volume and ease of styling without sacrificing softness as reported by the models.

crosslinked polydimethylsiloxane available from Dow Corning, Midland, Mich. IDPI polyurethane is a silicone polyurethane obtained from Alzo, Sayreville, N.J.

Examples D and E were designed to give greater softness to the hair. Examples F, G, H and I were designed to tame and control curly, thick or frizzy hair.

The following Salon Blitz Testing table is a summary of the results from a salon test conducted. The benchmark for these studies was a frizz taming product sold in the North American market. These data indicated that the HIPE formulation Example H outperformed the benchmark formulation in dispensing, application and in its ability to deliver hair body as reported by the models.

Test 3—Salon Blitz

Salon Blitz utilized female frizz product users as the panelists. A professional hair stylist applied the test product to half of the head and the benchmark product to the other side of the panelist's head. Once product has been applied, the stylist distributed the product evenly and left on the hair, keeping both sides separated. The panelists then dried and styled their own hair. A questionnaire was provided to each panelist asking them to rate (on a 9 point scale) hair characteristics for both the left and right side of the head. Higher values for key characteristics such as softness and fullness indicated a higher intensity for these attributes and therefore better performance on the hair. Approximately 20 panelists were recruited for each test product evaluation. Results for this test are shown in Table 2.

Examples of Conditioner and Frizz Tamer Products

| Composition | D Weight percent | E Weight percent | F Weight percent | G Weight percent | H Weight percent | I Weight percent |
|---|---|---|---|---|---|---|
| Oil Phase | | | | | | |
| DC 5225C | 5 | 5 | 4 | 7 | 5 | 3 |
| DC 200, 10 cst | 0 | 0 | 0.5 | 4 | 4 | 4 |
| DC 200, 5 cst | 3 | 3 | 3 | 0 | 0 | 0 |
| DC 200, 1.5 cst | 2 | 2 | 2 | 4 | 0 | 0 |
| DC 245 | 0 | 0 | 4 | 0 | 2 | 4 |
| Permethyl 101A | 0 | 0 | 0 | 0 | 0 | 2 |
| Fragrance | 0.25 | 0.25 | 0.30 | 0.25 | 0.25 | 0.25 |
| DC-2-9040, 16% | 0 | 0 | 1.5 | 0 | 0 | 0 |
| IDPI Polyurethane | 0 | 0.22 | 0 | 0 | 0 | 0 |
| Aqueous Phase | | | | | | |
| Hydroxyethylcellulose | 0 | 0 | 0 | 0 | 0 | 1.0 |
| Deionized Water | 86.45 | 85.23 | 80.52 | 80.55 | 84.45 | 81.45 |
| Soft water | 0 | 0 | 0 | 0 | 0 | 0 |
| Dicetyldimonium chloride, 30% | 3.00 | 0 | 0 | 0 | 0 | 0 |
| Preservative | 0.30 | 0.30 | 0.29 | 0.30 | 0.30 | 0.30 |
| Sodium Chloride | 0 | 4.00 | 3.89 | 3.90 | 4.00 | 4.00 |
| Total | 100 | 100 | 100 | 100 | 100 | 100 |
| Combing force (gm force) | NA | 35.5 | 37.2 | NA | NA | NA |

Permethyl 101A is a hydrocarbon available from Presperse, Inc., South Plainfield, N.J. DC-2-9040, 16% is a

TABLE 2

Salon testing of Example H versus a leading commercial frizz control product.

| Attribute Intensity | Frizz Benchmark- a commercial product | Example H |
|---|---|---|
| Ease of Dispensing | 2.9 | 7.7* |
| Ease of Application | 5.5 | 8.3* |
| Overall liking | 6.3 | 6.6 |
| Less frizzies | 2.9 | 4.0 |
| Softness | 7.4 | 7.8 |
| Fullness | 6.6 | 7.1 |
| Bounce | 6.2 | 6.4 |
| More Flat/Limp | 3.6 | 3.0 |

*90% Confidence Level.

Example A as a Leave-in Conditioner

Test 4 was similar to the salon application described in Test 2.

TABLE 3

Half-head Salon Testing versus Competitive Leave-in Conditioner.

| Attribute Intensity | Leave-in Benchmark | Example A |
|---|---|---|
| Overall liking | Equal | Equal |
| Ease of wet combing | Control | Advantage |
| Manageability | Control | Advantage |
| Body | Control | Advantage |

Example A presented distinct advantages in wet combing, manageability and body versus a competitive leave-in conditioner benchmark.

These formulations were found to have improved the stylability of the hair when left in the hair when compared to typical gel or leave-in conditioner.

Examples of Extra Body Conditioner Formulations or Skin Care Formulations

| Composition | P Weight percent | Q Weight percent | R Weight percent | S Weight percent |
|---|---|---|---|---|
| Oil Phase | | | | |
| DC 3225C or DC 5225C | 4.00 | 4.00 | 0 | 0 |
| DC 5180C, 49%* | 0 | 0 | 0.40 | 0.40 |
| DC 200, 10 cst | 0 | 1.00 | 1.00 | 1.00 |
| DC 200, 5 cst | 6.00 | 1.00 | 1.00 | 1.00 |
| DC 200, 1.5 cst | 2.00 | 2.00 | 3.60 | 0 |
| DC 200, 1–2 cst | 0 | 2.00 | 2.00 | 1.80 |
| DC 200, 0.65 cst | 0 | 2.00 | 2.00 | 1.80 |
| Fragrance | 0.25 | 0.25 | 0.25 | 0.25 |
| Aqueous Phase | | | | |
| Deionized Water | qs | qs | qs | Qs |
| Soft water | 84.75 | 84.75 | 84.75 | 84.75 |
| Sodium Chloride | 3.00 | 3.00 | 3.00 | 3.00 |
| Total | 100 | 100 | 100 | 100 |

*49% Dimethicone copolyol supplied by Dow Corning, Midland, Michigan.

Salon Testing

The following Salon Blitz Testing table is a summary of the results from a series of salon tests conducted. The benchmark for these studies is the best selling commercial Examples of Styling Conditioners

| Composition | J Weight percent | K Weight percent | L Weight percent | M Weight percent | N Weight percent | O Weight percent |
|---|---|---|---|---|---|---|
| Oil Phase | | | | | | |
| DC 5225C | 2 | 5 | 5 | 5 | 5 | 5 |
| DC 200, 10 cst | 0 | 0 | 0 | 0 | 0 | 0 |
| DC 200, 5 cst | 3 | 0 | 3 | 2 | 2 | 2 |
| DC 200, 1.5 cst | 0 | 2 | 2 | 3 | 3 | 3 |
| DC 245 | 4 | 3 | 0 | 0 | 0 | 0 |
| DC 200, 0.65 cst | 0 | 1 | 0 | 0 | 0 | 0 |
| Permethyl 101A | 1 | 0 | 0 | 0 | 0 | 0 |
| Fragrance | 0.25 | 0.25 | 0.25 | 0.25 | 0.25 | 0.25 |
| Aqueous Phase | | | | | | |
| Deionized Water | 0 | 84.95 | 69.70 | 79.15 | 83.13 | 82.65% |
| Soft water | 84.05 | 0 | 0 | 0 | 0 | 0 |
| Hydroxyethylcellulose | 0.40 | 1.00 | 0 | 0 | 0 | 0 |
| Copolymer 845, 20% | 1.00 | 2.50 | 0 | 0 | 1.00 | 1.00 |
| Styleze CC-10, 10% | 0 | 0 | 15.00 | 0 | 0 | 0 |
| Gafquat 755N, 20% | 0 | 0 | 0 | 5.00 | 0 | 0 |
| PVP/VA | 0 | 1.00 | 0 | 0 | 2.00 | 0 |
| PVP | 0 | 0 | 0 | 0 | 0 | 2.00 |
| Polyquaternium-4 | 0 | 0 | 0 | 0 | 0 | 0.25 |
| Preservative | 0.30 | 0.30 | 0.30 | 0.30 | 0.30 | 0.30 |
| Potassium Chloride | 4.00 | 0 | 0 | 0 | 0 | 0 |
| Sodium Chloride | 0 | 0 | 0 | 0 | 0 | 0 |
| Total | 100 | 100 | 100 | 100 | 100 | 100 | extra body conditioner in the North American market. These data indicated that the HIPE formulation (Example P) outperformed the benchmark formulation in both overall conditioning and in its ability to deliver hair body as reported by the models.

Test 5—Salon Blitz

Salon Blitz utilized female conditioner users as the panelists. A professional hair stylist applied the test product to half of the head and the benchmark product to the other side of the panelist's head. Once product has been applied, the stylist distributed the product evenly and rinsed it out taking care to keeping both sides separated. The panelists then dry and style their own hair. A questionnaire was provided to each panelist asking them to rate (on a 9 point scale) hair characteristics (e.g. conditioning and body) for both the left and right side of the head. Higher values for key characteristics such as conditioning or body indicates a higher intensity for these attributes and therefore better performance on the hair. 20 panelists were recruited for each test product evaluation. Results for this test are shown in Table 4.

TABLE 4

Salon testing of Extra Body Conditioner examples P versus benchmark conditioner.

| Attribute | Example P | Benchmark- a commercial product | Difference |
|---|---|---|---|
| Overall Liking | 6.47 | 5.63 | +0.84 |
| Wet Feel | 6.37 | 5.58 | +0.79 |
| Wet Detangling | 6.89 | 6.26 | +0.63 |
| Combing | 6.26 | 6.26 | 0.00 |
| Styling | 5.78 | 6.00 | −0.22 |
| Coating | 5.26 | 5.74 | −0.48 |
| Conditioning | 5.37 | 5.00 | +0.37 |
| Softness | 5.84 | 5.68 | +0.16 |
| Body | 5.5 | 5.05 | +0.45 |
| Bounce | 5.21 | 4.83 | +0.38 |
| Volume | 5.32 | 4.89 | +0.43 |

The above table shows that Example P delivered body without affecting conditioning performance. The results suggest that example P outperformed the benchmark conditioner in many areas. Without being held to this view, it is postulated that the enhanced overall liking, wet feel detangling, softness, body, bounce and volume may be attributed to the lack of fatty alcohol materials which may build up on the hair and weigh the hair down.

The above compositions may also be utilized as skin care products such as lotions, gels and shaving cream.

Examples of Skin Compositions

| Composition | T Weight percent | U Weight percent | V Weight percent | W Weight percent | X Weight percent | Y Weight percent |
|---|---|---|---|---|---|---|
| Oil Phase | | | | | | |
| DC 5225C | 8 | 10.00 | 7.00 | 4.00 | 4.00 | 4.00 |
| DC 200, 10 cst | 0 | 0 | 4.00 | 0 | 0 | 0 |
| DC 345 | 13 | 7.00 | 0 | 0 | 0 | 0 |
| DC 200, 1.5 cst | 0 | 0 | 4.00 | 6.50 | 6.50 | 6.50 |
| DC 200, 0.65 cst | 0 | 0 | 0 | 0 | 0 | 0 |
| Isopropyl myristate | 0 | 7.00 | 0 | 0 | 0 | 0 |
| Neutralizing agent | 0 | qs | 0 | 0 | 0 | 0 |
| Fragrance | 0.20 | 0.20 | 0.20 | 0.20 | 0.20 | 0.20 |
| Octyl methoxy cinnamate | 0 | 0 | 0 | 0 | 0 | 1.00 |
| Cetyl dimethicone Copolyol | 0 | 0 | 0 | 0 | 0.10 | 0 |
| Aqueous Phase | | | | | | |
| 2-hydroxy stearic acid | 1.00 | 6.00 | 1.00 | 1.00 | 1.00 | 1.00 |
| Propylene glycol | 15 | 0 | 0 | 0 | 0 | 0 |
| Deionized Water | qs | qs | qs | qs | qs | qs |

-continued

Examples of Skin Compositions

| Composition | T Weight percent | U Weight percent | V Weight percent | W Weight percent | X Weight percent | Y Weight percent |
|---|---|---|---|---|---|---|
| Polysorbate-20, 97% | 7.00 | 0 | 0 | 0 | 0 | 0 |
| Ethanol (SD-40, 200 Proof) | 7.00 | 0 | 0 | 0 | 0 | 0 |
| Sodium Chloride | 0 | 2.00 | 4.00 | 3.00 | 3.00 | 3.00 |
| Total | 100 | 100 | 100 | 100 | 100 | 100 |

In the above table compositions T and U are controls.

Test 6—Spreading, Greasiness and Residue Panel

The skin products were evaluated by rubbing 0.2 g of product onto a watch glass and spreading the sample to create a smooth film. The spreading ease and greasiness was then ranked. A similar amount of material was also rubbed onto the skin and then ranked in order of fastest to slowest absorption (residue). The smooth after feel was also ranked. It is noted that a lower number indicates more desirable performance aesthetics. Examples T and U were more tacky, sticky and undesirable on the skin when compared to Examples V and W. Examples V and W dried without a tacky transition phase. It was found that examples V and W also have the benefit of leaving behind very little residue and no greasy/oily after feel. In addition, examples T and U were more difficult to wash off the skin.

TABLE 5

Skin Cream Test Results.

| Composition | Spreading Ease* | Greasiness | Residue | Smooth Afterfeel |
|---|---|---|---|---|
| T | 4 | 4 | 4 | 4 |
| U | 3 | 3 | 3 | 3 |
| V | 2 | 2 | 2 | 2 |
| W | 1 | 1 | 1 | 1 |

*A lower number for key characteristics indicates a lower intensity for these attributes and indicates better performance.

It should be understood that the present disclosure has been made only by way of preferred embodiment and that numerous changes in detail of construction, combination and arrangement of parts may be resorted to without departing from the spirit and scope of the invention herein claimed.

What is claimed is:

1. A hair care composition which comprises:
   (I) an external oil phase which further comprises i.) a mixture of non-volatile and volatile silicone oils, and ii.) a silicone surfactant; and
   (II) an internal aqueous phase that is about 80% to about 95% of the composition; and
   (III) a water soluble or oil soluble holding polymer; and wherein said composition substantially lacks a fatty alcohol.

2. A composition according to claim 1 wherein the silicone surfactant is present from about 2% to about 15%.

3. A composition according to claim 1 wherein the non-volatile silicone is present from about 0.01% to about 10%.

4. A composition according to claim 1 wherein the volatile silicone component is present at about 0.01% to about 10%.

5. A composition according to claim 1 further comprising an inorganic or organic salt in the aqueous phase.

6. A composition according to claim 1 further comprising an anionic, cationic or amphoteric or nonionic surfactant.

7. A composition according to claim 1 further comprising an oligosaccharide or polysaccharide.

8. A composition according to claim 1 further comprising a thickener.

9. A composition according to claim 1 further comprising a topically active compound.

10. A composition according to claim 1 in which the nonvolatile silicone has an atmospheric boiling point of greater than about 250° C.

11. A composition according to claim 1 in which the volatile silicone has an atmospheric boiling point from about 20° C. to about 250° C.

12. A composition according to claim 2 wherein the silicone surfactant is a dimethylsiloxane of the formula:

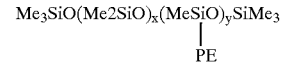

wherein Me represents methyl, EO represents ethyleneoxy, PO represents 1,2-propyleneoxy, x and y are 1 or greater, m and n are 0 or greater, and the molecular weight of the PE unit must be greater than 1000, and Z can be either hydrogen or a lower alkyl radical.

13. A composition according to claim 2 wherein the silicone surfactant is an alkyl dimethicone copolyol of the formula:

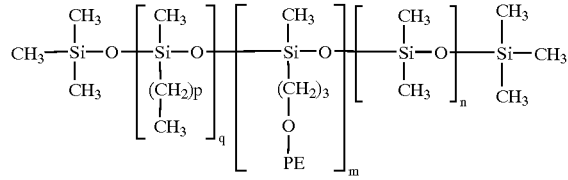

wherein p is a numeral from 7 through 17; q is a numeral from 1 through 100; m is a numneral from 1 through 40; n is a numeral from 0 through 200; and PE is $(C_2H_4O)_a(C_3H_6O)_b$—H having a molecular weight of about 250 to about 2000, wherein a and b are selected such that the weight ratio of $C_2H_4O/C_3H_6O$ is from 100/0 to 20/80.

14. A composition according to claim 1 comprising a mixture of volatile silicone oils containing one volatile silicone oil in the range of about 1.4 to about 1.6 and one volatile silicone oil in the range of about 0.5 to about 0.7 cst.

15. A composition according to claim 14 wherein one volatile silicone oil has a viscosity of about 0.5 cst and the other volatile silicone oil has a viscosity of about 1.5 cst.

16. A composition according to claim 5, wherein the salt is an inorganic or organic salt wherein the salt is sodium chloride, potassium chloride, sodium citrate, sodium lactate, aluminum zirconium glycinate, aluminum chlorohydrate, salts of amino acids, or mixtures thereof.

17. A composition according to claim 6, wherein the anionic surfactant is selected from the group consisting of alkyl sulphates, alkyl aryl sulphonates, alkyl ether sulphonates, alkyl ether sulfates, alkyl sulfonates, alkyl isothionates, alkyl succinates, alkyl sulphosuccinates, alkyl sarcosinates, alkyl phosphates, alkyl carboxylates, alkyl ether carboxylates and alpha-olefin sulphonates; and their sodium, magnesium, ammonium, and mono-, di-, and tri-ethanolamine salts, and mixtures thereof.

18. A composition according to claim 6, wherein the nonionic surfactant is linear or branched, ethoxylated, or propoxylated, or mixtures thereof.

19. A composition according to claim 6, wherein the amphoteric surfactant is selected from the group of betaine, cetyl betaine, cocamidopropylbetaine, cocamidopropyl hydroxysultaine, coco-betaine, coco/oleamidopropyl betaine, coco-sultaine, decyl betaine, hydrogenated tallow betaine, isostearamidopropyl betaine, lauramidopropyl betaine, lauryl betaine, lauryl sultaine, myristidopropyl betaine, myristyl betaine, oleamidopropyl betaine, oleamidopropyl hydroxysultaine, oleyl betaine, palamidopropyl betaine, palmitaridopropyl betaine, ricinoleamidopropyl betaine, stearamidopropyl betaine, tallowamidoproyl betaine, tallowamidopropyl hydroxysultaine, wheat germamidopropyl betaine, cocampho carboxyglycinate, laurampho carboxyglycinate, or mixtures thereof.

20. A composition according to claim 6, wherein the cationic surfactant has the structure:

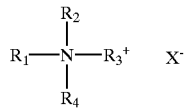

wherein $R_1$ is an alkyl group including from about 8 to about 20 carbon atoms; $R_2$ is selected from the group consisting of an alkyl group including from about 8 to about 20 carbon atoms, a hydrogen atom, a methyl group, an ethyl group, a hydroxymethyl group and a hydroxyethyl group; $R_3$ is selected from the group consisting of a benzyl group, a hydrogen group, a methyl group, an ethyl group, a hydroxymethyl group and a hydroxyethyl group; $R_4$ is selected from the group consisting of a hydrogen atom, a methyl group, an ethyl group, a hydroxymethyl group and a hydroxyethyl group; and x is an anion selected from the group consisting of chloride, methosulfate, ethosulfate, nitrate, bromide, tosylate, acetate, or phosphate, and mixtures thereof, and optionally two of $R_1$, $R_2$, $R_3$ and $R_4$ form a heterocylic nitrogen containing moiety, selected from the group consisting of morpholine and pyridine.

21. A composition according to claim 20, wherein the cationic surfactant has the structure:

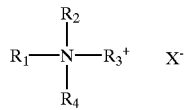

and the quaternary nitrogen and two of $R_1$, $R_2$, $R_3$, and $R_4$, form a heterocyclic nitrogen-containing moiety, selected from the group consisting of morpholine and pyridine.

22. A composition according to claims 1, wherein the holding polymer is selected from the group consisting of: vinyl and acrylic-based resins, a vinyl pyrrolidone/dimethylaminoethyl methacrylate copolymer, a PVP/DMAPA Acrylates Copolymer, Polymer 1189 (Terpolymer of Vinyl pyrrolidone/Vinyl Caprolactam and 3-( N-Dimethylaminopropyl) Methacrylamide, Quaternium-23, the butyl ester of PVM/MA copolymer, PVP K-30 to K-90, Octylacrylamide/Acrylates/Butylaminoethyl Methacrylate Copolymer, an Acrylates/Octylacrylamide Copolymer, VA/Crotonates/Vinyl Neodecanoate Copolymer and an Octylacrylamide/Acrylates/Butylaminoethylmethacrylate Copolymer, Polyether Polyurethanes, acrylamide copolymers, acrylamide/sodium acrylate copolymer, acrylate/ammonium methacrylate copolymer, acrylate copolymers, acrylic/acrylate copolymers, acrylic esters and methacrylic esters copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, ammonium acrylate copolymers, ammonium vinyl acetate/acrylate copolymers, AMP acrylate/diacetoneacrylamide copolymers, AMPD acrylate/diacetoneacrylamide copolymers, butylated PVP, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, diglycol/cyclohexaned imethanol/Isophthalates/sulfoisophthalates AQ 55S polymer, diglycol/isophthalates/sulfoisophthalates copolymer AQ29S polymer, dodecanedioic acid/cetearyl alcohol/glycol copolymer, ethyl ester of PVM/MA copolymer, isopropyl ester of PVM/MA copolymer, Graft-copoly (diemthylsiloxane iso-butyl methacrylate), Graft-copoly (IBMA;MEFOSEA/PDMS), methacrylates/acrylates copolymer/amine salt, methacryloyl ethyl betaine/methacrylate copolymers, octylacryl-amide/acrylate/butylaminoethyl methacrylate copolymers, octylacrylamide/acrylate copolymers, phthalic anhydride/glycerin/g lycidyl decanoate copolymer, phthalic/trimellitic/glycol copolymers, polyacrylamide, polyacrylamidomethylpropane sulfonic acid, polybutylene terephthalate, polyethylacrylate, polyethylene, polymethacrylamidopropyl trimonium chloride, polyquaternium-1, polyquaternium-2, polyquaternium-4, polyquaternium-5, polyquaterium-6, polyquaterium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-24, polyquaternium-28, polyquaternium-37, polyquaternium-46, polyvinyl acetate, polyvinyl butyral, polyvinyl imidazolinium acetate, polyvinyl methyl ether, ethyl ester of poly (methyl vinyl ether/maleic acid, butyl ester of poly (methyl vinyl ether/maleic acid, PVM/MA copolymer, PVP, PVP/acrylates copolymer, PVP/dimethylaminoethylmethacrylate terpolymer, PVP/eicosene copolymer, PVP/ethyl methacrylate/methacrylic acid copolymer, PVP/hexadecane copolymer, PVP/NA copolymer, PVP/VA/vinyl propionate copolymer, PVP/vinyl acetate copolymer, PVP/vinyl acetate/itaconic acid copolymer, quaternium-23, shellac, sodium acrylate/vinyl alcohol copolymer, sodium carrageenan, starch diethylaminoethyl ether, stearylvinylether/maleic anhydride copolymer, sucrose benzoate/sucrose acetate isobutyrate/butyl benzyl phthalate copolymer, styrene/PVP copolymer, sucrose benzoate/sucrose acetate isobutyrate/butyl benzyl phthalate/methyl methacrylate copolymer, sucrose benzoate/sucrose acetate iso-butyrate copolymer, Tricontanyl PVP, vinyl acetate/crotonate copolymers, vinyl acetate/crotonic acid copolymer, vinyl acetate/butyl maleate/Isobornyl acetate copolymer, vinyl acetate/crotonic acid/methacryloxybenzophenone-1 copolymer, vinyl acetate/crotonic acid/vinyl neodecanoate copolymer, vinyl caprolactam/PVP/Dimethylaminoethyl methacrylate copolymer, and mixtures thereof.

23. A composition according to claim 7, wherein the oligosaccharide or polysaccharide is selected from the group: methyl cellulose, carboxymethyl cellulose, hydroxy propyl methyl cellulose, hydroxyethyl cellulose, hydroxypropyl cellulose, and ethyl hydroxyethyl cellulose, dextrans, Kitamer PC, a chitosan carboxylate and Kytamer L, a chitosan lactate, Gafquat HS-100, Polyquaternium-28, polyquaternium-4, polyquatemium-10, sodium alginate, agarose, amylopectins, amyloses, arabinans, arabinogalactans, arabinoxylans, carrageenans, gum arabic, cellulose derivatives such as methylcellulose, hydroxypropylmethylcellulose, hydroxyethyl cellulose, carboxymethylcellulose, carboxymethylguar gum, carboxymethyl(hydroxypropyl)guar gum, hydroxyethylguar gum, hydroxypropylguar gum, cationic guar gum, chondroitins, chitins, chitosans, cocodimonium hydroxypropyl oxyethyl cellulose, colominic acid [poly(N-acetylneuraminic acid], corn starch, curdlan, dermatin sulfate, furcellarans, dextrans, cross-linked dextrans known as dextranomer (Debrisan), dextrin, emulsan, flaxseed saccharide (acidic), galactoglucomannans, galactomannans, glucomannans, glycogens, guar gum, or hydroxyethylstarch, hydroxypropylstarch, hydroxypropylated guar gums, gellan gum, glucomannans, gellan, gum ghatti, gum karaya, gum tragacanth (tragacanthin), heparin, hyaluronic acid, inulin, keratan sulfate, konjac mannan, latinarans, laurdimonium hydroxypropyl oxyethyl cellulose, liposan, locust bean gum, imannans, nigeran, nonoxylnyl hydroxyethyl cellulose, okra gum, oxidized starch, pectic acids, pectins, polydextrose, potato starch, protopectins, psyllium seed gum, pullulan, sodium hyaluronate, steardimonium hydroxyethyl cellulose, raffinose, rhamsan, tapioca starch, welan, levan, scleroglucan, stachyose, succinoglycan, wheat starch, xanthan gum, xylans, xyloglucans, and mixtures thereof.

24. A composition according to claim 8, wherein the thickener is selected from the group: Acrylates/Steareth-20 Itaconate Copolymer, Acrylates/Ceteth-20 Itaconate Copolymer, PVM/MA, Acrylates/steareth-20 methacrylate copolymer, acrylamide/sodium acrylate copolymer, acrylate copolymer, acrylic acid/acrylonitrogens copolymer, Acrylic/acrylate copolymer, Ammonium acrylates/acrylonitrogens copolymer, Quaternium-18 Bentonite, Sodium salt of crosslinked poly(acrylic acid), Stearalkonium Bentonite, Claytone, Quaternium-18 Hectorite, Stearalkonium Hectorite, acrylamide/sodium acrylate copolymer, Poly (acrylic acid), polyquaternium-18, polyquaternium-27, polyquaternium-31, polyquaternium-37, trihydroxystearin; Dimethylaminoethyl methacrylamide and acrylamide copolymer, Acrylic polymer anionic or cationic thickening agents, and mixtures, thereof.

25. A composition according to claim 9 wherein the topically active compound has the structure:

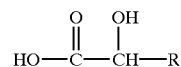

where R is a hydrogen or aliphatic chain ranging from 1 to 28 carbons.

26. A composition according to claim 9 wherein the topically active compound is selected from the group of Para-aminobenzoic acid (PABA), PABA esters, glyceryl PABA, amyldimethyl PABA, octyldimethyl PABA, cinnamates, octyl methoxycinnamate, cinoxate, benzophenones, benzophenone-4, oxybenzone, sulisobenzone, salicylates, octyl salicylate, anthranilates, methyl anthranilate, and mixtures thereof.

27. A composition according to claim 9 wherein the topically active compound is selected from the group of hair growth promoters such as glucarolactams, glucarolactones, and diacylglycerols; and mixtures thereof.

28. A hair product comprising the composition of claim 1 in a form selected from the group consisting of shampoo, conditioner, spray, mousse, gel, foam, styling conditioner, hair serum, lotion, creme, and pomade.

29. A method for treating hair which comprises contacting said hair with a composition according to claim 1.

30. A composition according to claim 1, which comprises an internal aqueous phase that is about 85% to about 90% of the composition.

* * * * *